United States Patent [19]

Stroppolo et al.

[11] Patent Number: 5,693,312

[45] Date of Patent: Dec. 2, 1997

[54] PHARMACEUTICAL COMPOSITION HAVING ANALGESIC ACTIVITY

[75] Inventors: Federico Stroppolo, Pregassona, Switzerland; Daniele Bonadeo, Varese, Italy; Luigi Viganò, Curiglia, Switzerland; Annibale Gazzaniga, Milan, Italy

[73] Assignee: Zambon Group S.p.A., Vicenza, Italy

[21] Appl. No.: 470,143

[22] Filed: Jun. 6, 1995

Related U.S. Application Data

[63] Continuation of Ser. No. 219,309, Mar. 29, 1994, abandoned.

[30] Foreign Application Priority Data

Mar. 26, 1993 [IT] Italy ................. MI93A0582

[51] Int. Cl.$^6$ ................. A61K 9/46; A61K 9/20; A61K 31/19; A61K 33/10
[52] U.S. Cl. ................. 424/44; 424/717; 514/557; 514/568; 514/960
[58] Field of Search ................. 424/44, 717; 514/557, 514/568, 960

[56] References Cited

U.S. PATENT DOCUMENTS

| | | | |
|---|---|---|---|
| 3,904,682 | 9/1975 | Fried et al. | |
| 4,279,926 | 7/1981 | Bruzzese et al. | 424/316 |
| 4,344,929 | 8/1982 | Bonsen et al. | 424/15 |
| 4,587,249 | 5/1986 | Sunshine et al. | |
| 4,689,218 | 8/1987 | Gazzaniga et al. | 424/43 |
| 4,834,966 | 5/1989 | Gazzaniga et al. | 424/43 |
| 4,937,080 | 6/1990 | Appelgren et al. | 424/490 |
| 5,019,563 | 5/1991 | Hunter et al. | 514/50 |
| 5,053,396 | 10/1991 | Blass | 514/45 |
| 5,055,306 | 10/1991 | Barry et al. | 424/482 |
| 5,262,179 | 11/1993 | Gregory et al. | 424/489 |

FOREIGN PATENT DOCUMENTS

| | | |
|---|---|---|
| 0 398 288 | 11/1990 | European Pat. Off. |
| 0 486 045 | 5/1992 | European Pat. Off. |
| 0 486 046 | 5/1992 | European Pat. Off. |
| 2 602 141 | 2/1988 | France |

OTHER PUBLICATIONS

Megory et al. U.S. 5262179 (Nov. 16, 1993).
Barry et al. U.S. 5055306 (Oct. 08, 1991).
Appelgren et al. U.S. 4937080 (Jun. 28, 1990).
Gazzaniga et al. (II) U.S. 4834966 (May 30, 1989).
Gazzaniga et al. (I) U.S. 4689218 (Aug. 25, 1989).
Blass U.S. 5053346 (Oct. 01, 1991).
Chemical Abstracts, vol. 103, No. 8, 1985, p. 336, AN 103:59148c.
A. Fini et al, "Dissolution Profiles of NSAID Carboxylic Acids and Their Salts with Different Counter Ions," *Pharm. Acta Helv.*, vol. 60, No. 2 (1985), pp. 58–62.

*Primary Examiner*—Shep K. Rose
*Attorney, Agent, or Firm*—Oblon, Spivak, McClelland, Maier & Neustadt, P.C.

[57] ABSTRACT

Pharmaceutical compositions having analgesic activity containing (S)-2-(6-methoxy-2-naphthyl)-propionic acid as active ingredient and arginine, useful for the preparation of pharmaceutical forms for oral route, are described.

27 Claims, No Drawings

PHARMACEUTICAL COMPOSITION HAVING ANALGESIC ACTIVITY

This application is a continuation of application Ser. No. 08/219,309, filed on Mar. 28, 1994, now abandoned.

The present invention relates to a pharmaceutical composition with analgesic activity and, more particularly, it relates to a pharmaceutical composition containing (S)-2-(6-methoxy-2-naphthyl) propionic acid as active ingredient, useful for the preparation of pharmaceutical formulations for oral use.

(S)-2-(6-methoxy-2-naphthyl)propionic acid and its salts with pharmaceutically acceptable organic or inorganic bases have been described for the first time in U.S. Pat. No. 3,904,682 (Syntax Corporation).

Subsequently, the salts of some non-steroidal antiinflammatory drugs (NSAIDs) with basic aminoacids have been described in U.S. Pat. No. 4,279,926 (SPA-Società Prodotti Antibiotici S.p.A.) to be particularly useful for the preparation of injectable pharmaceutical formulations because of their solubility in water giving neutral aqueous solutions.

Since several years, (S)-2-(6-methoxy-2-naphthyl) propionic acid, hereinafter indicated with the International Nonproprietary Name (INN) Naproxen, is used in therapy as free acid or as a salt, especially sodium or piperazine salt, for its analgesic, antiinflammatory and antipyretic properties (Merck Index, XI ed., No. 6337, page 1014).

Naproxen is orally administered at daily doses of 500–1500 mg. The maximum plasmatic concentration is generally between 49 and 90 µg/ml and it is reached in about two hours [Verbruggen and Moll, Nonclassical oral formulations of NSAIDs, page 391—"Therapeutic Applications of NSAIDs", edited by J. P. Famaey, Harold E. Paulus, Marcel Dekker Inc., New York, (1992)].

It is clear that the need of pharmaceutical compositions able to anticipate the onset of the pharmacological effect of non-steroidal antiinflammatory drugs is highly felt, particularly in the analgesic therapy.

U.S. Pat. No. 4,587,249 (Analgesic Associates) describes an analgesic and antiinflammatory composition containing an association of caffeine and a non-steroidal antiinflammatory drug able to increase the analgesic and antiinflammatory effect and to anticipate its onset.

Both caffeine and non-steroidal antiinflammatory drugs are commonly used in analgesic therapy.

U.S. Pat. No. 4,834,966 (Zambon S.p.A.) describes Ibuprofen water-soluble compositions containing 33–46% by weight of Ibuprofen, 34–51% by weight of L-arginine and 9–29% by weight of sodium bicarbonate which allow to obtain an increase of Ibuprofen maximum plasmatic concentration and a remarkable anticipation of the onset time of the analgesic effect.

The molar ratio between arginine and Ibuprofen must be from 1.1 to 1.5 while the weight ratio between sodium bicarbonate and Ibuprofen is from 0.25 to 0.75.

We have now surprisingly found a pharmaceutical composition containing Naproxen and arginine able to significantly anticipate the onset of the analgesic effect after opal administration.

Therefore, object of the present invention is a pharmaceutical composition useful for the preparation of pharmaceutical formulations for opal use consisting of a mixture of Naproxen and arginine in a molar ratio from 1:0.8 to 1:1.5 and of an optional pharmaceutically compatible auxiliary basic substance in a molar ratio up to 0.7 with respect to Naproxen, so that, if dissolved in water, the resultant aqueous solution has a pH value from 7.5 to 9.0. Naproxen is used in the mixture in the form of free acid.

Arginine is preferably L-arginine.

The molar ratio between Naproxen and arginine is preferably between 1:0.8 and 1:1.2, still more preferably it is 1:1.1.

Specific examples of pharmaceutically compatible auxiliary basic substances are inorganic bases such as sodium or potassium bicarbonate, sodium or potassium carbonate, disodium or dipotassium phosphate, sodium phosphate ($Na_3PO_4$) or potassium phosphate ($K_3PO_4$) or organic bases such as sodium or potassium citrate, sodium or potassium tartrate, N-methylglucamine, D-glucamine or glucosamine and mixtures thereof.

Exclusively for practical and economical reasons, sodium or potassium bicarbonate is preferably used.

Preferably, the molar ratio between Naproxen and the pharmaceutically compatible auxiliary basic substance, when present, is comprised from 1:0.2 to 1:0.4.

The pharmaceutical composition object of the present invention allows to obtain a significant anticipation of the onset of the analgesic effect after oral administration and it is particularly useful for the preparation of pharmaceutical formulations for oral use such as tablets, effervescent tablets, granulates, powders, syrups and solutions.

The peculiar characteristic of the composition object of the present invention is arginine.

It is worth underlining that arginine can be present also in stoichiometric default with respect to the molar amount of Naproxen. Furthermore, the pharmaceutical composition of the invention is hydrosoluble giving aqueous solutions with a pH from 7.5 to 9.0.

It is clear to the man skilled in the art that the pH value of the aqueous solution is mainly due to the presence of arginine and, consequently, when arginine is in a molar excess, the addition of the auxiliary basic substance may not be necessary.

The choice of the optional pharmaceutically compatible auxiliary basic substance has also the purpose of improving the characteristic of the finished pharmaceutical formulation.

For example, the use of an inorganic base such as sodium or potassium bicarbonate improves the rheological characteristics of the mixture making it particularly suitable for the granulation and the compression.

The preparation of the pharmaceutical compositions object of the present invention is carried out by mixing according to usual techniques.

As already underlined, the compositions object of the present invention allow to obtain a significant anticipation of the onset of the analgesic effect with respect to formulations on the market containing sodium Naproxen (example 16).

A significant anticipation of the onset of the analgesic effect due to an increase of the maximum plasmatic concentration is obtained with the compositions of the present invention also when compared to compositions containing an equivalent amount of Naproxen in the form of arginine salt (example 17).

It is worth noting that the AUC (Area Under Curve) is substantially the same in the compositions of the invention and in formulations containing sodium Naproxen present on the market or in the formulation containing only the arginine salt of Naproxen.

From a practical point of view, this means that the analgesic effect begins in advance (generally after some minutes) and lasts longer.

It is not yet clear the mechanism through which the compositions of the invention give rise to such a remarkable anticipation of the onset of the analgesic effect of Naproxen with respect to commercial formulations of sodium Naproxen.

This result does not appear to be dependent on either partial total salification of Naproxen so that the dissolution step is hastened at gastric level because it is known that the sodium salt of Naproxen is much more soluble, and consequently allows a much higher dissolution speed at gastric level, than the arginine salt [A. Fini et al., Pharm. Acta Helv., 60(2), 58–62, (1985)].

Tentatively, it could be argued that arginine has an active role at gastric level in the step of absorption of Naproxen in the form of free acid.

On the other hand, the compositions object of the present invention behave differently at gastric level in comparison with compositions containing the salt of Naproxen with arginine.

In fact, the presence of a slight excess of arginine or of small amounts of a pharmaceutically compatible auxiliary basic substance, according to the invention, allows to significantly increase the percentage of dissolved active ingredient (Naproxen) in the stomach in comparison with the gastric dissolution of the simple arginine salt (Example 18).

For the preparation of pharmaceutical formulations such as tablets, effervescent tablets, granulates, powders, syrups and solutions, further excipients suitable for the pharmaceutical use such as, for example, sweetening agents, flavoring agents, effervescent mixtures and coloring agents, can be added to the composition object of the present invention.

Preferably, the pharmaceutical formulations will contain an amount of Naproxen equal to 125, 250 or 500 mg.

The preparation of the pharmaceutical formulations is carried out according to conventional techniques of granulation, compression and dilution.

In order to better illustrate the present invention, without limiting it, the following examples are now given.

EXAMPLE 1

A mixture having the following composition

| Naproxen | 500 g |
|---|---|
| L-Arginine | 416 g | was prepared by mixing the two powders, separately sieved, in a mixer up to homogeneity.

The aqueous solution obtained by dissolving 0.916 g of the resultant mixture in 200 ml of water has pH=8.2.

EXAMPLE 2

A mixture having the following composition

| Naproxen | 500 g |
|---|---|
| L-Arginine | 416 g | was prepared by wet granulation and the granulate was dried in a static oven.

EXAMPLE 3

A mixture having the following composition

| Naproxen | 500 g |
|---|---|
| L-Arginine | 302.5 g |
| Sodium bicarbonate | 73 g | was prepared by mixing the three powders, separately sieved, in a mixer up to homogeneity.

EXAMPLE 4

A mixture having the following composition

| Naproxen | 500 g |
|---|---|
| L-Arginine | 302.5 g |
| Sodium bicarbonate | 73 g | was prepared by wet granulation and the granulate was dried in a static oven.

EXAMPLE 5

A mixture having the following composition

| Naproxen | 500 g |
|---|---|
| L-Arginine | 378.2 g |
| Sodium bicarbonate | 36.5 g | was prepared by mixing the three powders, separately sieved, in a mixer up to homogeneity.

EXAMPLE 6

A mixture having the following composition

| Naproxen | 500 g |
|---|---|
| L-Arginine | 378.2 g |
| Sodium bicarbonate | 36.5 g | was prepared by wet granulation and the granulate was dried in a static oven.

EXAMPLE 7

A mixture having the following composition

| Naproxen | 500 g |
|---|---|
| L-Arginine | 560 g | was prepared by mixing the two powders, separately sieved, in a mixer up to homogeneity.

Alternatively, the mixture was granulated with water and the granulate was dried in a static oven.

EXAMPLE 8

A mixture having the following composition

| Naproxen | 500 g |
|---|---|
| L-Arginine | 378.2 g |
| Sodium bicarbonate | 54.7 g | was prepared by wet granulation and the granulate was dried in a static oven.

EXAMPLE 9

Saccharose (1939 g), sodium saccharin (20 g), aspartame (25 g) and mint flavour (100 g) were added to a mixture prepared as described in Example 1.

The resultant mixture was shared into about 1000 sachets having the following composition (3 g in all)

| | | |
|---|---|---|
| Naproxen | 500 | mg |
| L-Arginine | 416 | mg |
| Saccharose | 1939 | mg |
| Sodium saccharin | 20 | mg |
| Aspartame | 25 | mg |
| Mint flavour | 100 | mg |

EXAMPLE 10

Saccharose (1939 g), sodium saccharin (20 g), aspartame (25 g) and mint flavour (100 g) were added to a granulate prepared as described in Example 2.

The resultant mixture was shared into about 1000 paper-aluminum-polyethylene sachets having the following composition (3 g in all)

| | | |
|---|---|---|
| Naproxen | 500 | mg |
| L-Arginine | 416 | mg |
| Saccharose | 1939 | mg |
| Sodium saccharin | 20 | mg |
| Aspartame | 25 | mg |
| Mint flavour | 100 | mg |

Alternatively, the mixture was shared into sachets containing 1.5 g or 0.75 g, corresponding to 250 or 125 mg of Naproxen respectively.

EXAMPLE 11

Microcrystalline cellulose (116 g), crosslinked polyvinylpyrrolidone (40 g) and magnesium stearate (8 g) were added to a granulate prepared as described in Example 2 and the resultant mixture was mixed up to homogeneity.

The mixture was compressed obtaining tablets (1.080 g) each containing 500 mg of Naproxen.

Alternatively, tablets weighing 0.540 g or 0.270 g each and containing 250 mg or 125 mg of Naproxen respectively were prepared.

EXAMPLE 12

Sorbitol (1939 g), sodium saccharin (20 g), aspartame (60 g) and apricot flavour (100 g) were added to a granulate prepared as described in Example 4.

The resultant mixture was shared into about 1000 paper-aluminum-polyethylene sachets at the rate of 3 g each.

Alternatively, the mixture was shared into sachets containing 1.5 g or 0.75 g, corresponding to 250 or 125 mg of Naproxen respectively.

EXAMPLE 13

Xylitol (900.3 g), sodium saccharin (25 g), aspartame (60 g) and anise flavour (100 g) were added to a mixture prepared as described in Example 6.

The resultant mixture was shared into about 1000 sachets having the following composition (2 g in all)

| | | |
|---|---|---|
| Naproxen | 500 | mg |
| L-Arginine | 378.2 | mg |
| Sodium bicarbonate | 36.5 | mg |
| Xylitol | 900.3 | mg |
| Sodium saccharin | 25 | mg |
| Aspartame | 60 | mg |
| Anise flavour | 100 | mg |

EXAMPLE 14

Sodium bicarbonate (800 g), sodium bitartrate (900 g), aspartame (40 g) and flavour (100 g) were added to a mixture prepared as described in Example 7

The resultant mixture was compressed thus obtaining effervescent tablets (2.9 g) each containing 500 mg of Naproxen.

Alternatively, effervescent tablets weighing 1.45 g and each containing 250 mg of Naproxen were prepared.

EXAMPLE 15

Sodium bicarbonate (800 g), sodium bitartrate (900 g), saccharose (1140 g) and flavour (100 g) were added to a mixture prepared as described in Example 7.

The resultant mixture was compressed obtaining effervescent tablets (4 g) each containing 500 mg of Naproxen.

Alternatively, effervescent tablets weighing 2 g or 1 g each and containing 250 or 125 mg of Naproxen respectively were prepared.

EXAMPLE 16

Aqueous solutions of a granulate prepared as described in Example 1, containing 500 mg of Naproxen (treatment A) and of a sodium Naproxen commercial granulate, containing an equivalent amount of active ingredient (treatment B) were administered with a single dose by oral route to 12 subjects aged 32.5±4.05.

Each subject was apparently healthy, in particular as far as the renal, hepatic and hematopoietic functions were concerned.

Each subject received both preparations in two treatment sessions carried out two weeks apart, randomizing the order of administration.

During each session, basal samples of venous blood were drawn (in the morning) from each fasting subject, prior to oral administration of the preparation A or B. Further venous blood samples were also drawn 0.25, 0.50, 0.75, 1, 2, 3, 4, 8, 12 and 24 hours after treatment.

The analytical determination of Naproxen in the blood samples was carried out following the HPLC method hereinafter described.

Chromatographic conditions:

Apparatus HP 1090 L equipped with a diode array detector

HPLC column Hypersil ODS (5 μm, 100×2.1 mm) plus a precolumn Hypersil ODS (5 μm, 20×2.1 mm)

Mobile phase: $Na_2HPO_4 \cdot 2H_2O$ 0.03M (corrected to pH 3 with $H_3PO_4$:$CH_3OH$=48:52)

Flow: 0.5 ml/min

Column temperature: 40° C.

Wavelength: 230.4 nm

Internal standard: a solution of Flurbiprofen in methanol (0.15 mg/ml)

The internal standard (0.2 ml) was added to plasma (0.1 ml). The whole was mixed and allowed to rest.

After 30 minutes, it was centrifuged at 4500 rounds per 10 minutes. The clear surnatant (10 μl) was injected into the HPLC system. Under the described operative conditions, the retention times were as follows:

Naproxen=3.8 minutes

Internal standard=8.7 minutes

The obtained results are reported in the following table 1.

TABLE 1

Mean plasma concentration of Naproxen after oral treatment with a solution of a pharmaceutical composition according to the present invention (treatment A) and after oral treatment with a commercial composition (treatment B).
Administered dose: 500 mg of active ingredient.
Plasma concentration of Naproxen (μg/ml)

| Treatment | Time after treatment (hours) | | | | | | | | | |
|---|---|---|---|---|---|---|---|---|---|---|
| | 0.25 | 0.50 | 0.75 | 1 | 2 | 3 | 4 | 8 | 12 | 24 |
| A | 52.2 | 58.6 | 69.8 | 61.3 | 58.6 | 53.3 | 48.4 | 37.3 | 29.9 | 18.0 |
| B | 13.0 | 22.0 | 31.1 | 43.5 | 61.8 | 63.4 | 56.0 | 39.9 | 32.4 | 18.0 |

Pharmacokinetic parameters

The following parameters were calculated and evaluated. The area under curve of Naproxen plasma concentration from time "zero" to time 24 hours ($AUC_{obs}=AUC_{o \to 24h}$) expressed as $\mu g \times h \times ml^{-1}$ was calculated following the trapezoidal rule method (Gibaldi M. and Perrier D., "Pharmacokinetics", pages 293-296, Marcel Dekker Inc., New York 1975).

The area under curve of Naproxen plasma concentration from time "zero" to "infinite" ($AUC_{tot}$) was calculated by the following formula $$AUC_{o \to 24h} + AUC_{24h \to \infty}$$

wherein $$AUC_{24h \to \infty} = \frac{\text{concentration at 24h}}{K_e}$$

and $K_e$=elimination constant

The mean peak time expressed in hours was obtained by averaging the individual peak times.

The mean plasma concentration ($C_{max}$) expressed as μg/ml was calculated by averaging the single peak values of the concentrations. The lag time (hours) is the delay between the drug administration and the beginning of the absorption.

The values of the above specified pharmacokinetic parameters are reported in the following table 2.

TABLE 2

Pharmacokinetic parameters obtained after oral treatment with a solution of a pharmaceutical composition according to the invention (preparation A) and after oral treatment with a solution of a commercial composition (preparation B).
Administered dose: 500 mg of active ingredient.

| Pharmacokinetic parameters | Preparation A | Preparation B |
|---|---|---|
| $AUC_{obs}$ (μg × h × ml$^{-1}$) | 812 | 835 |
| $AUC_{tot}$ (μg × h × ml$^{-1}$) | 1192 | 1041 |
| Peak time (hours) | 1.22 | 2.63 |
| $C_{max}$ (μg/ml) | 75.4 | 70.6 |
| Lag time (hours) | 0.02 | 0.12 |

From the values reported in the table, it is evident that the compositions object of the present invention show a remarkable anticipation of the onset of the analgesic effect.

In fact, the peak time and the lag time are significantly lower than those of a commercial composition of sodium Naproxen and the maximum concentration ($C_{max}$) is higher.

EXAMPLE 17

Aqueous solutions of a granulate prepared as described in Example 6, containing 250 mg of Naproxen, arginine and sodium bicarbonate (treatment A) and of a granulate, containing an equivalent amount of active ingredient but in the form of arginine salt and without sodium bicarbonate (treatment B) were administered with a single dose by opal route to 6 healthy adult male volunteers in fasting conditions.

The solutions were administered in both cases according to an open, balanced, randomized, cross-over design. A wash out period of 7 days was observed between the treatments.

For each treatment, a basal sample of venous blood was drawn from each fasting subject, prior to opal administration of the preparation A or B. Further venous blood samples were also drawn 0.17, 0.33, 0.5, 0.75, 1, 1.5, 2, 2.5, 3, 4, 8, 12, 24, 30 and 36 hours after treatment.

The analytical determination of Naproxen in the blood samples was carried out by HPLC with U.V. detection.

Chromatographic conditions:

HPLC column Hypersil ODS (5 μm, 100×2.1 mm) plus a precolumn Hypersil ODS (5 μm, 20×2.1 mm)

Mobile phase: $Na_2HPO_4 \cdot 2H_2O$ 0.03M (corrected to pH 3 with $H_3PO_4:CH_3OH=48:52$)

Flow: 0.5 ml/min

Column temperature: 40° C.

Wavelength: 230.4 nm

Internal standard: a solution of Flurbiprofen in methanol (0.15 mg/ml)

The internal standard (0.2 ml) was added to plasma (0.1 ml). The whole was mixed and allowed to rest at 4° C.

After 30 minutes, it was centrifuged at 4500 rounds per 10 minutes. The clear surnatant (0.1 ml) was injected into the HPLC system. The obtained results are reported in the following table 3.

TABLE 3

Mean plasma concentration of Naproxen after oral treatment with a solution of a pharmaceutical composition according to the present invention (treatment A) and after oral treatment with a composition containing only Naproxen in the form of arginine salt (treatment B).
Administered dose: 250 mg of active ingredient.
Naproxen plasma concentration (μg/ml)

| Time after treatment (hours) | Treatment A | Treatment B |
|---|---|---|
| 0.17 | 20.0 | 19.1 |
| 0.33 | 28.5 | 27.7 |
| 0.5 | 30.4 | 29.3 |
| 0.75 | 35.2 | 31.2 |
| 1 | 33.6 | 30.6 |
| 1.5 | 32.0 | 29.5 |
| 2 | 30.6 | 29.3 |

TABLE 3-continued

Mean plasma concentration of Naproxen after oral treatment with a solution of a pharmaceutical composition according to the present invention (treatment A) and after oral treatment with a composition containing only Naproxen in the form of arginine salt (treatment B). Administered dose: 250 mg of active ingredient.

Naproxen plasma concentration (μg/ml)

| Time after treatment (hours) | Treatment A | Treatment B |
|---|---|---|
| 2.5 | 28.5 | 27.9 |
| 3 | 26.5 | 26.7 |
| 4 | 25.1 | 24.2 |
| 8 | 19.8 | 18.7 |
| 12 | 16.6 | 15.0 |
| 24 | 10.8 | 9.02 |
| 30 | 6.65 | 6.31 |
| 36 | 3.60 | 4.20 |

Pharmacokinetic parameters

The following parameters were calculated and evaluated. The area under curve of Naproxen plasma concentration from time "zero" to time 36 hours ($AUC_{obs} = AUC_{o \to 36h}$) expressed as μg×h×ml$^{-1}$ was calculated following the trapezoidal rule method (Gibaldi M. and Perrier D., "Pharmacokinetics", pages 293–296, Marcel Dekker Inc., New York 1975).

The area under curve of Naproxen plasma concentration from time "zero" to "infinite" ($AUC_{tot}$)) was calculated by the following formula $$AUC_{o36h \to} + AUC_{36h \to \infty}$$

wherein $$AUC_{36h \to \infty} = \frac{\text{concentration at 36h}}{K_e}$$

and $K_e$=elimination constant

The mean peak time expressed in hours was obtained by averaging the individual peak times.

The mean plasma concentration ($C_{max}$) expressed as μg/ml was calculated by averaging the single peak values of the concentrations. The elimination half-life (t½) expressed in hours.

The values of the above specified pharmacokinetic parameters are reported in the following table 4.

TABLE 4

Pharmacokinetic parameters obtained after oral treatment with a solution of a pharmaceutical composition according to the invention (preparation A) and after oral treatment with a solution of a composition containing only an equivalent amount of Naproxen in the form of arginine salt (preparation B). Administered dose: 250 mg of active ingredient.

| Pharmacokinetic parameters | Preparation A | Preparation B |
|---|---|---|
| $AUC_{obs}$ (μg × h × ml$^{-1}$) | 570 | 493 |
| $AUC_{tot}$ (μg × h × ml$^{-1}$) | 592 | 535 |
| Peak time (hours) | 0.70 | 0.68 |
| $C_{max}$ (μg/ml) | 36.8 | 32.4 |
| t½(hours) | 11.8 | 12.0 |

From the values reported in the table, it is evident that a composition containing Naproxen, arginine and sodium bicarbonate in the ratio 1:1:0.2, according to the present invention, allows to obtain a maximum plasmatic concentration ($C_{max}$) meaningfully higher than that of a composition containing only the arginine salt of Naproxen. This means that the analgesic effect of the composition of the present invention is greater and faster.

EXAMPLE 18

Aqueous solutions (100 ml) of a granulate prepared as described in Example 8, containing 200 mg of Naproxen, arginine and sodium bicarbonate (preparation A) and of a granulate, containing an equivalent amount of active ingredient but in the form of arginine salt and without sodium bicarbonate (preparation B) were treated with HCl 0.03N (30 ml) in order to simulate the acidity produced by the gastric juice.

The resultant suspensions were filtered through a Millipore filter membrane (0.8 μm).

A quantitative determination of Naproxen present in the starting suspension, in the filtered solution and in the residue on the filter was carried out according to the following procedure.

Apparatus: Hewlett-Packard liquid chromatograph (mod. 1050 and mod. 1090A) with U.V. detector at changeable wavelength. Hewlett-Packard data recorder system (mod.3359A).

Column: Hewlett-Packard RP-18, 200×4.6 nm, 5 μm.

Chromatographic conditions:

mobile phase: tetrabutylammonium hydroxide 0.005M corrected to pH 7.0 with phosphoric acid:acetonitrile= 62:38 flow: 2.0 ml/minutes wavelength: 270 nm eluent temperature: room temperature column temperature: 40° C.

injected volume: 10 μl retention time: 2.2 minutes

Preparation of the standard solution: Naproxen (200 mg) was dissolved in the mobile phase up to volume (100 ml). An aliquot (5 ml) of the resultant solution was further diluted with the mobile phase up to volume (20 ml).

Preparation of the sample solution: the starting suspension and the solution obtained after filtering the starting suspension were suitably diluted with the mobile phase in order to obtain a theoretical Naproxen concentration as equal as possible to the concentration of the standard solution (about 0.5 mg/ml). The filtered residue was dissolved with the mobile phase up to a volume corresponding as much as possible to the theoretical Naproxen concentration of the standard solution.

The resulting detected amounts of Naproxen are reported in the following table 5.

TABLE 5

Amounts of Naproxen dissolved under simulated gastric conditions obtained from a granulate according to the invention (preparation A) and from a granulate containing an equivalent amount of active ingredient (preparation B).

| | Naproxen amount (%) | |
|---|---|---|
| | Preparation A | Preparation B |
| Starting suspension | 100 | 100 |
| Filtered solution | 28.45 | 6.15 |
| Filtered residue | 71.55 | 93.85 |

From the above data it clearly results that, under conditions simulating the gastric acidity, the composition of the present invention allows the dissolution of a higher amount of active ingredient than a composition containing an equivalent amount of Naproxen in the form of arginine salt.

What we claim is:

1. A pharmaceutical composition, consisting essentially of:
   (a) (S)-2-(6-methoxy-2-naphthyl)propionic acid;
   (b) arginine; and
   (c) a sufficient amount of a pharmaceutically acceptable auxiliary base, such that said pharmaceutical composition, when dissolved in water, affords an aqueous solution having a pH of from 7.5 to 9.0;
   wherein:
   (i) said (S)-2-(6-methoxy-2-naphthyl)propionic acid and said arginine are present in relative amounts such that the molar ratio of (S)-2-(6-methoxy-2-naphthyl)propionic acid to arginine is from 1:0.8 to 1:1.5; and
   (ii) said pharmaceutically acceptable auxiliary base and said (S)-2-(6-methoxy-2-naphthyl)propionic acid are present in relative amounts such that the molar ratio of pharmaceutically acceptable auxiliary base to (S)-2-(6-methoxy-2-naphthyl)propionic acid is from 0:1 to 0.7:1.

2. The pharmaceutical composition of claim 1, wherein said arginine is L-arginine.

3. The pharmaceutical composition of claim 1, wherein said molar ratio of (S)-2-(6-methoxy-2-naphthyl)propionic acid to arginine is from 1:0.8 to 1:1.2.

4. The pharmaceutical composition of claim 1, wherein said molar ratio of (S)-2-(6-methoxy-2-naphthyl)propionic acid to arginine is 1:1.1.

5. The pharmaceutical composition of claim 1, wherein said pharmaceutically acceptable auxiliary base is selected from the group consisting of sodium bicarbonate, potassium bicarbonate, sodium carbonate, potassium carbonate, disodium phosphate, dipotassium phosphate, sodium phosphate ($Na_3PO_4$), potassium phosphate ($K_3PO_4$), sodium citrate, potassium citrate, sodium tartrate, potassium tartrate, N-methylglucamine, D-glucamine, glucosamine, and mixtures thereof.

6. The pharmaceutical composition of claim 1, wherein said pharmaceutically acceptable auxiliary base is sodium bicarbonate or potassium bicarbonate.

7. The pharmaceutical composition of claim 1, wherein said molar ratio of pharmaceutically acceptable auxiliary base to (S)-2-(6-methoxy-2-naphthyl)propionic acid is from 0.2:1 to 0.4:1.

8. The pharmaceutical composition of claim 1, wherein said (S)-2-(6-methoxy-2-naphthyl)propionic acid is present in an amount of 125 mg.

9. The pharmaceutical composition of claim 1, wherein said (S)-2-(6-methoxy-2-naphthyl)propionic acid is present in an amount of 250 mg.

10. The pharmaceutical composition of claim 1, wherein said (S)-2-(6-methoxy-2-naphthyl)propionic acid is present in an amount of 500 mg.

11. The pharmaceutical composition of claim 1, further consisting essentially of a pharmaceutically acceptable excipient.

12. A pharmaceutical composition, consisting essentially of:
    (a) (S)-2-(6-methoxy-2-naphthyl)propionic acid;
    (b) arginine; and
    (c) a sufficient amount of a pharmaceutically acceptable auxiliary base, such that said pharmaceutical composition, when dissolved in water, affords an aqueous solution having a pH of from 7.5 to 9.0;
    wherein:
    (i) said (S)-2-(6-methoxy-2-naphthyl)propionic acid and said arginine are present in relative amounts such that the molar ratio of (S)-2-(6-methoxy-2-naphthyl)propionic acid to arginine is from 1:1 to 1:08; and
    (ii) said pharmaceutically acceptable auxiliary base and said (S)-2-(6-methoxy-2-naphthyl)propionic acid are present in relative amounts such that the molar ratio of pharmaceutically acceptable auxiliary base to (S)-2-(6-methoxy-2-naphthyl)propionic acid is up to 0.7:1.

13. The pharmaceutical composition of claim 12, wherein said arginine is L-arginine.

14. The pharmaceutical composition of claim 12, wherein said pharmaceutically acceptable auxiliary base is selected from the group consisting of sodium bicarbonate, potassium bicarbonate, sodium carbonate, potassium carbonate, disodium phosphate, dipotassium phosphate, sodium phosphate ($Na_3PO_4$), potassium phosphate ($K_3PO_4$), sodium citrate, potassium citrate, sodium tartrate, potassium tartrate, N-methylglucamine, D-glucamine, glucosamine, and mixtures thereof.

15. The pharmaceutical composition of claim 12, wherein said pharmaceutically acceptable auxiliary base is sodium bicarbonate or potassium bicarbonate.

16. The pharmaceutical composition of claim 12, wherein said molar ratio of pharmaceutically acceptable auxiliary base to (S)-2-(6-methoxy-2-naphthyl)propionic acid is from 0.2:1 to 0.4:1.

17. The pharmaceutical composition of claim 12, wherein said (S)-2-(6-methoxy-2-naphthyl)propionic acid is present in an amount of 125 mg.

18. The pharmaceutical composition of claim 12, wherein said (S)-2-(6-methoxy-2-naphthyl)propionic acid is present in an amount of 250 mg.

19. The pharmaceutical composition of claim 12, wherein said (S)-2-(6-methoxy-2-naphthyl)propionic acid is present in an amount of 500 mg.

20. The pharmaceutical composition of claim 12, further consisting essentially of a pharmaceutically acceptable excipient.

21. A pharmaceutical composition, consisting essentially of:
    (a) (S)-2-(6-methoxy-2-naphthyl)propionic acid; and
    (b) arginine; and
    wherein:
    (i) said (S)-2-(6-methoxy-2-naphthyl)propionic acid and said arginine are present in relative amounts such that the molar ratio of (S)-2-(6-methoxy-2-naphthyl)propionic acid to arginine is at least 1:1.5 and said arginine is present in a sufficient molar excess over said (S)-2-(6-methoxy-2-naphthyl)propionic acid such that said pharmaceutical composition, when dissolved in water, affords an aqueous solution having a pH of from 7.5 to 9.0.

22. The pharmaceutical composition of claim 21, wherein said arginine is L-arginine.

23. The pharmaceutical composition of claim 21, wherein said molar ratio of (S)-2-(6-methoxy-2-naphthyl)propionic acid and arginine is 1:1.1.

24. The pharmaceutical composition of claim 21, wherein said (S)-2-(6-methoxy-2-naphthyl)propionic acid is present in an amount of 125 mg.

25. The pharmaceutical composition of claim 21, wherein said (S)-2-(6-methoxy-2-naphthyl)propionic acid is present in an amount of 250 mg.

26. The pharmaceutical composition of claim 21, wherein said (S)-2-(6-methoxy-2-naphthyl)propionic acid is present in an amount of 500 mg.

27. The pharmaceutical composition of claim 21, further consisting essentially of a pharmaceutically acceptable excipient.

* * * * *

UNITED STATES PATENT AND TRADEMARK OFFICE
CERTIFICATE OF CORRECTION

PATENT NO. : 5,693,312
DATED : December 2, 1997
INVENTOR(S) : Federico STROPPOLO, et al.

It is certified that error appears in the above-identified patent and that said Letters Patent is hereby corrected as shown below:

On the title page, item [63] should be:

--[63]   Continuation of Ser. No. 219,309, Mar. 28, 1994, abandoned.--

Signed and Sealed this

Twenty-fourth Day of February, 1998

Attest:

BRUCE LEHMAN

*Attesting Officer*   *Commissioner of Patents and Trademarks*